(12) United States Patent
Rey et al.

(10) Patent No.: US 6,280,789 B1
(45) Date of Patent: Aug. 28, 2001

(54) PROCESS FOR PREPARATION OF HYDROXYAPATITE COATINGS

(75) Inventors: Christian Rey, Castanet Tolosan; Xavier Ranz, Montauban, both of (FR)

(73) Assignee: Biocoatings S.r.l., Solignano (IT)

( * ) Notice: Subject to any disclaimer, the term of this patent is extended or adjusted under 35 U.S.C. 154(b) by 0 days.

(21) Appl. No.: 09/180,059

(22) PCT Filed: Apr. 21, 1997

(86) PCT No.: PCT/IT97/00089

§ 371 Date: Jun. 28, 1999

§ 102(e) Date: Jun. 28, 1999

(87) PCT Pub. No.: WO97/41273

PCT Pub. Date: Nov. 6, 1997

(30) Foreign Application Priority Data

Apr. 30, 1996 (IT) .............................. PR96A0021

(51) Int. Cl.$^7$ .............................. B05D 1/18; A61L 27/00
(52) U.S. Cl. ...................... 427/2.27; 427/2.26
(58) Field of Search .............. 427/2.26, 2.27

(56) References Cited

U.S. PATENT DOCUMENTS

| | | | |
|---|---|---|---|
| 5,068,122 | * 11/1991 | Kokubo et al. | 427/2 |
| 5,188,670 | * 2/1993 | Constantz | 118/667 |
| 5,441,536 | * 8/1995 | Aoki et al. | |
| 5,478,237 | * 12/1995 | Ishizawa | 433/201.1 |
| 6,207,218 | * 3/2001 | Layrolle et al. | 427/2.27 |

OTHER PUBLICATIONS

Chemical Abstracts, vol. 124, No. 20, May 13, 1996 (Columbux, Ohio); Abstract No. 268002.*

* cited by examiner

*Primary Examiner*—Fred J. Parker
*Assistant Examiner*—Jennifer Kolb
(74) *Attorney, Agent, or Firm*—Darby & Darby

(57) ABSTRACT

Coatings of scarcely crystalline carbonated hydroxyapatite are deposited on metallic or ceramic substrates, by immersing the substrates in a solution containing calcium phosphate and bicarbonate ions, with a molar ratio calcium/phosphate from 0.8 to 2 and a pH from 6.8 to 8.0. Subsequently, the solution is heated to 50–80° C., thus raising the pH and causing a spontaneous deposition of carbonated hydroxyapatite on the substrates. The obtained coatings are highly biocompatible, osteoconductive, bioactive and biodegradable, and can be utilized in structures used for preparing orthopaedic and dental prostheses and implants.

13 Claims, No Drawings

PROCESS FOR PREPARATION OF HYDROXYAPATITE COATINGS

DESCRIPTION

The present invention relates to a process for coating a substrate with a coating of carbonated hydroxyapatite, to a structure comprising a substrate coated with a coating obtainable by said process, as well as an orthopaedic or dental prosthesis or implant comprising said structure.

It is known that mineral components of animal bones and teeth consist essentially of calcium phosphates and in particular of phosphates belonging to the class of hydroxyapatite, which is represented by the formula $Ca_{10}(PO_4)_6(OH)_2$, wherein the molar ratio calciun ions to phosphate ions is 1.67.

It is also known that hydroxyapatites forming animal bones and teeth (also called "biological hydroxyapatites") are non-stoichiometric hydroxyapatites, which contain extraneous ions, such as carbonate, sodium, potassium, magnesium and fluorine, and are characterized by a molar ratio calcium ions to phosphate ions lower than 1.67.

Synthetic hydroxyapatites can be used for preparing orthopaedic and dental prostheses and implants. In order to be suitable for said use, synthetic hydroxyapatites must have structure and composition similar to those of biological hydroxyapatites, must be non-toxic with respect to the animal body, must be biocompatible (i.e. compatible with the animal body without giving place to adverse reactions with respect to the body functions), osteoconductive (i.e. capable of strongly adhering to the animal bone and promoting its healing and growth), bioresorbable or biodegradable (i.e. capable of being dissolved in the animal body) and bioactive (i.e. capable of facilitating cellular activity and repair of living tissues).

In the preparation of prostheses and implants, synthetic hydroxyapatites are used for example in the form of coatings which are deposited on metallic or ceramic substrates. Such coatings are obtained by dry processes at high temperature, such as plasma-spraying, which however cause decomposition of the material, formation of other phases and presence of impurities in the coatings; moreover, the thus obtained coatings are made of crystals having rather great sizes, and have rather small specific surface area and surface reactivity; consequently, protein adsorption, which is necessary to promote attachment of osteoblast cells and their proliferation, is insufficient. Hence, long term stability, osteoconductivity, bioresorbability and bioactivity of said coatings are unsatisfactory.

Processes for obtaining hydroxyapatite coatings by deposition from solutions containing calcium and phosphate ions have been proposed. However, such processes are slow, complicated and difficult to be controlled. Moreover, they provide coatings which have scarce adhesion to the substrate, are unsatisfactory in terms of composition and crystalline structure and, therefore, do not comply with the requirements of osteoconductivity, bioresorbability and bioactivity. An object of the present invention is therefore that of providing a process which is easy to be carried out and controlled, and allows the formation of hydroxyapatite coatings having excellent adhesion to the substrate, scarce crystallinity (i.e. being made of crystals of rather small sizes), high specific surface area and surface reactivity, and complying in an excellent way with the requirements of biocompatibility, osteoconductivity, bioresorbability and bioactivity.

This and other objects are achieved by the present invention which provides a process for coating a substrate with a coating consisting essentially of carbonated hydroxyapatite.

By the term "carbonated hydroxyapatite" a hydroxyapatite is meant, wherein phosphate and/or hydroxy ions are partially replaced by $HCO_3$ bicarbonate ions.

The process of the present invention comprises:
(a) immersing the substrate to be coated in an aqueous solution containing calcium ions in a concentration from 1 to less 3.8 mmoles/liter, phosphate ions in a concentration from 1 to less 3.8 mmoles/liter and bicarbonate ions in a concentration from 0.08 to 0.25 moles/liter, with a molar ratio calcium ions to phosphate ions from 0.8 to 2.0, a pH from 6.8 to 8.0 and a temperature lower than 50° C.;
(b) heating at least the portion of the solution in contact with the substrate to a temperature from 50 to 80° C. until having a pH greater than 8;
(c) maintaining the substrate in contact with the heated supersaturated alkali solution obtained in step (b), thus causing formation of a carbonated hydroxyapatite coating to take place spontaneously directly at the contact with the surface of the substrate; and
(d) taking the substrate off the solution, after the requested thickness of coating has been obtained, and subjecting the coating to drying.

Another object of the present invention is a structure comprising a substrate consisting of metallic or ceramic material coated with a coating obtainable by the above mentioned process.

A further object of the present invention is an orthopaedic or dental prosthesis or implant comprising said structure.

Substrates, to which the process of the present invention can be applied, can be made of metallic or ceramic material. Preferably the substrate surface must have a certain porosity and/or roughness. If necessary, porosity and/or roughness of the surface can be increased by means of appropriate treatments, such as laser treatment, sanding or plasma-spraying treatment.

By way of example, the substrates can be made of a metal selected from titanium, titanium alloys, zirconium, zirconium alloys, vanadium and vanadium alloys, or a material coated with a coating of said metals or metal alloys.

Other examples are substrates made of a ceramic material selected from hydroxyapatite, fluoridated hydroxyapatite and other calcium phosphates, or substrates consisting of a metallic material coated with a coating of said ceramic materials, said coating having been obtained by a dry process at high temperature, e.g. by plasma-spraying.

By the term "fluoridated hydroxyapatite" a hydroxyapatite is meant, wherein hydroxy ions have been partially replaced by fluorine ions in order to reduce the dissolution and degradation rate of the hydroxyapatite at the contact with other substances which are present in the animal body.

The Applicants have found that the process of the present invention is particularly suitable and advantageous for coating substrates, which have been previously coated with hydroxyapatite by plasma-spraying.

In particular the Applicants have found that multilayer structures comprising a metal substrate, coated with a first coating of metallic material, preferably the same metallic material as that of the substrate, with a second coating of hydroxyapatite, optionally fluoridated, and with a third coating of carbonated hydroxyapatite, the latter having been obtained by the process of the present invention, are characterized by excellent mechanical properties and other properties, such as biocompatibility, osteoconductivity, bioresorbability and bioactivity. Consequently, said multilayer structures can be advantageously used for making orthopaedic and dental prostheses and implants.

Particularly advantageous are multilayer structures wherein both said first metallic coating (with a thickness of preferably 30–100 μm) and said second hydroxyapatite coating are obtained by plasma-spraying under vacuum or in inert atmosphere. Preferably, before depositing said second coating, porosity and/or roughness of the metal surface can be increased by appropriate treatments of the above mentioned types.

The aqueous solution of step (a) is a solution which is stable and can be easily prepared at ambient temperature and handled without a particular care.

In step (a) the solution is utilized preferably at ambient temperature and can be prepared by dissolving any compounds of the requested ions in deionized water. Preferably calcium ions are introduced in the form of calcium nitrate $Ca(NO_3)_2$, phosphate ions in the form of ammonium hydrogenphosphate $(NH_4)_2HPO_4$ and bicarbonate ions in the form of sodium bicarbonate $NaHCO_3$.

Other ions, such as for example fluorine, sodium, potassium and magnesium, can optionally be added to the solution in order to improve some specific properties of the bioactive coating to be obtained.

Preferably the solution of step (a) contains calcium ions in a concentration from 1 to 2 mmoles/liter, phosphate ions in a concentration from 1 to 2 mmoles/liter and bicarbonate ions in a concentration from 0.10 to 0.18 moles/liter. More preferably the solution of step (a) contains calcium ions in a concentration from 1.4 to 1.8 mmoles/liter and phosphate ions in a concentration from 1.2 to 1.7 mmoles/liter.

The molar ratio calcium ions to phosphate ions in the solution of step (a) is preferably from 0.9 to 1.6.

The pH of the solution of step (a) is preferably from 7.2 to 7.6, more preferably about 7.4. The pH can be adjusted at the desired value by adding acidic solutions. By way of example, the solution which is utilized in step (a) can be obtained by preparing previously two concentrated solutions in deionized water, the former containing calcium ions (solution A) and the latter containing phosphate and bicarbonate ions (solution B), and by mixing subsequently solutions A and B in a bulk of deionized water, so as to reach the concentrations and proportions required by the process of the present invention.

In step (b) of the process of the present invention the solution is heated preferably to a temperature from 60 to 78° C., more preferably from 65 to 75° C., most preferably from 68 to 72° C. Said heating can be carried out by any known method.

The solution in steps (b) and (c) is preferably maintained under agitation, in order to homogenize the deposition at the substrate surface. Such agitation can be performed by agitating either the solution or the substrate to be coated or both. The Applicants have found that, by virtue of the retrograde solubility of hydroxyapatite (in the sense that hydroxyapatite is less soluble at high temperature than at low temperature) and thanks to the instability of the bicarbonate solution, which decomposes releasing carbon dioxide, said heating provides an increase of pH and a highly supersaturated alkali solution, which causes the precipitation of carbonated hydroxyapatite, in the form of crystallization nuclei, at the contact with the substrate surface.

Moreover, the Applicants have found that bicarbonate ions act as inhibitors of crystal growth and that the coating forming in step (c) of the process of the present invention has a scarcely crystalline structure, i.e. a structure characterized by crystals which contain defects, are not stoichiometric and have rather small dimensions.

Generally, the crystals of the coating obtained by the process of the present invention have a 10–40 nm length and a 3–10 nm width.

The Applicants have further found that the coating obtained by the process of the present invention adheres perfectly to the substrate and has very high specific surface area and surface reactivity.

The substrate is taken off from the solution as the coating has reached the desired thickness.

The time period by which the substrate is maintained immersed in the solution in step (c) is preferably from 3 minutes to 2 hours.

The thickness of the coating obtained by the process of the present invention is preferably from 1 to 10 μm and the bicarbonate ion concentration is preferably 10 to 22% by weight with respect to the total weight of the coating.

After the substrate has been taken off from the solution, the coating is dried, for instance in air.

The coatings obtained by the process of the present invention were subjected to various physico-chemical analyses as well as to in vitro and in vivo tests. All the results show that the coatings of the present invention are perfectly biocompatible, highly osteoconductive (i.e. they accelerate the bone ongrowth near to the implant), highly bioactive (i.e. they enhance remarkably the cell activity) and highly biodegradable (bioresorbable).

The following examples are offered to illustrate some embodiments of the invention, without limiting the scope of same.

EXAMPLE 1

Specimens consisting of disks (15 mm diameter, 3 mm thickness) made of a TA6V alloy (which is a titanium alloy containing 6% by weight vanadium), coated with a hydroxyapatite coating having 100–130 μm thickness, were prepared by the Italian company Flametal S.p.A., by plasma-spraying deposition, in inert argon and nitrogen atmosphere, using stoichiometric hydroxyapatite powder (i.e. with calcium to phosphate molar ratio of 1.67). Said specimens are utilized without having been subjected to any treatment for increasing porosity and/or roughness. A concentrated solution A is prepared by dissolving 4.57 g of $Ca(NO_3)_2$ (98% by weight purity) in 500 ml deionized water, thus obtaining a calcium ion concentration equal to 38 mmoles/liter. Then a solution B is prepared by dissolving 2.53 g of $(NH_4)_2HPO_4$ (99.5% by weight purity) in 500 ml deionized water, thus obtaining a phosphate ion concentration equal to 38 mmoles/liter.

Each of the two solutions A and B is diluted 5 times with deionized water, thus reaching a concentration of 7.6 mmoles/liter. Afterwards 10 g of $NaHCO_3$ are added to solution B and the pH of this solution is adjusted at 7.4 by adding diluted nitric acid.

200 ml of solution A and 200 ml of solution B thus obtained are diluted and mixed by pouring them in 600 ml of deionized water. In such a way a solution is obtained, which contains 1.52 mmoles/liter of calcium ions, 1.52 mmoles/liter of phosphate ions and 0.12 moles/liter of bicarbonate ions, wherein the calcium/phosphate molar ratio is equal to 1.

The pH of the solution is adjusted again at 7.4 and the specimens are immersed in the solution maintained at ambient temperature and under agitation.

Still maintaining the solution under agitation and agitating also the specimens, the solution is heated to 70° C., causing an increase of the pH up to 8.7 and a spontaneous precipitation-crystallization of carbonated hydroxyapatite at the contact of the surface of the specimens.

After 5 minutes from the start of precipitation, the specimens are taken off from the solution and dried in air. A very thin white layer having about 5 μm thickness has formed on the surface of the specimens.

EXAMPLE 2

Example 1 is repeated with the only difference that, instead of heating the entire mass of the solution, only the specimens are heated by high frequence heating. Moreover, a circulation system of the supersaturated solution is performed, in order to avoid heating of the entire solution and to cause that only the solution close to the substrates be heated to 70° C. Circulation and continuous renewal of the solution allows to control thickness and homogeneity of the coating.

After 5 minutes from the start of precipitation, a very thin white layer having about 8 μm thickness has formed on the surface of the specimens.

The coatings of both Example 1 and Example 2 were subjected to a series of characterizations.

Infrared spectrum adsorption analyses carried out with a Perkin-Elmer FTIR 1760 show that carbonated hydroxyapatite has formed in the coatings and by quantitative chemical analysis it has been determined that the bicarbonate ion concentration is 20% by weight with respect to the total weight of the coating.

X ray characterization carried out utilizing a CPS120 diffractometer of Inel and wavelength of cobalt (1.78897 Å) shows the presence of a scarcely crystalline structure similar to that of animal bones.

In the case of Example 1 the crystals have an average length of 15 nm and an average width of 5 nm. In the case of Example 2 the crystals have an average length of 13 nm and an average width of 4 nm.

Before the treatment according to the present invention, the specimens had been subjected to the same characterizations as those mentioned above. By comparing the results it has been determined that in the average the dimensions of the crystals of the coating deposited in the Examples 1 and 2 are 15 to 18% smaller than the crystals of the coatings deposited by plasma-spraying.

By comparing the measurements of specific surface area carried out with the BET method before and after the treatment of the present invention, it has been determined that after the treatment the specific surface area increased by 12–14%. Moreover, in vitro biological characterizations have been carried out according to AFNOR S91-145 and S91-142 standards (AFNOR=Association Francaise de Normalisation). Cellular behaviour of human osteoblasts as attachment density to the coating material, cytoplasmic aspect, cellular proliferation and biocompatibility in the treated specimens are remarkably improved in comparison with the untreated specimens. Moreover, no cytotoxicity of the coatings according to the present invention has been found.

What is claimed is:

1. A process for coating a substrate with a coating of a desired thickness consisting essentially of carbonated hydroxyapatite, which process comprises:

(a) immersing the substrate to be coated in an aqueous solution containing calcium ions in a concentration of from 1 to less than 3.8 mmoles/liter, phosphate ions in a concentration of from 1 to less than 3.8 mmoles/liter and bicarbonate ions in a concentration of from 0.08 to 0.25 moles/liter, with a molar ratio calcium ions to phosphate ions from 0.8 to 2.0, a pH from 6.8 to 8.0 and a temperature lower than 50° C.:

(b) heating at least the portion of the solution in contact with the substrate until the temperature reaches from 50 to 80° C. and the pH is greater than 8;

(c) maintaining the substrate in contact with the heated supersaturated alkali solution obtained in step (b), thus causing formation of a carbonated hydroxyapatite coating to take place spontaneously directly at the contact with the surface of the substrate; and (d) removing the substrate from the solution, after the desired thickness of coating has been obtained, and subjecting the coating to drying.

2. The process of claim 1, wherein the substrate to be coated consists of a ceramic or metallic material.

3. The process of claim 1, wherein the substrate to be coated consists of a ceramic material selected from the group consisting of hydroxyapatite, fluoridated hydroxyapatite and other calcium phosphates.

4. The process of claim 1, wherein the substrate to be coated consists of a metallic material selected from the group consisting of titanium, titanium alloys, zirconium, zirconium alloys, vanadium and vanadium alloys.

5. The process of claim 1, wherein the substrate to be coated is a coating of ceramic or metallic material, which has been previously deposited on a support.

6. The process of claim 1, wherein the substrate to be coated is a coating of hydroxyapatite, which has been previously deposited by plasma-spraying on a metallic support.

7. The process of claim 1, wherein the aqueous solution of step (a) contains calcium ions in a concentration from 1 to 2 mmoles/liter, phosphate ions in a concentration from 1 to 2 mmoles/liter and bicarbonate ions in a concentration from 0.10 to 0.18 moles/liter, and the molar ratio calcium ions to phosphate ions in said solution is from 0.9 to 1.6.

8. The process of claim 1, wherein the calcium ions are introduced into the aqueous solution of step (a) in the form of calcium nitrate $Ca(NO_3)_2$.

9. The process of claim 1, wherein the phosphate ions are introduced into the aqueous solution of step (a) in the form of ammonium hydrogenphosphate $(NH_4)_2HPO_4$.

10. The process of claim 1, wherein the bicarbonate ions are introduced into the aqueous solution of step (a) in the form of sodium bicarbonate $NaHCO_3$.

11. The process of claim 1, wherein the aqueous solution of step (a) is at a pH from 7.2 to 7.6 and at ambient temperature.

12. The process of claim 1, wherein the aqueous solution in step (b) is heated to a temperature from 60 to 78° C.

13. A structure comprising a substrate coated with a coating consisting essentially of carbonated hydroxyapatite by the process according to claim 1.

* * * * *

UNITED STATES PATENT AND TRADEMARK OFFICE
CERTIFICATE OF CORRECTION

PATENT NO.    : 6,280,789 B1
DATED         : August 28, 2001
INVENTOR(S)   : Christian Rey It is certified that error appears in the above-identified patent and that said Letters Patent is hereby corrected as shown below:

<u>Title page,</u>
Item [30], Foreign Application Priority Data, change "PR96A0021" should read -- PR96A000021--.

Signed and Sealed this

Sixteenth Day of July, 2002

*Attest:*

JAMES E. ROGAN
*Attesting Officer*   *Director of the United States Patent and Trademark Office*